United States Patent [19]
Lee et al.

[11] Patent Number: 5,786,478
[45] Date of Patent: Jul. 28, 1998

[54] PROCESS FOR PREPARING CYANOPYRAZINE

[75] Inventors: Young K. Lee; Chae-Ho Shin; Tae-Sun Chang; Dong-Ku Lee; Deug-Hee Cho, all of Taejon, Rep. of Korea

[73] Assignee: Korea Research Institute of Chemical Technology, Rep. of Korea

[21] Appl. No.: 519,534

[22] Filed: Aug. 25, 1995

[30] Foreign Application Priority Data

Aug. 26, 1994 [KR] Rep. of Korea ............ 94-21140

[51] Int. Cl.$^6$ ............................................. C07D 241/24
[52] U.S. Cl. ............................................. 544/336; 502/211
[58] Field of Search ............................. 544/336; 546/286

[56] References Cited

U.S. PATENT DOCUMENTS

| | | | |
|---|---|---|---|
| 3,555,021 | 1/1971 | Beutel et al. | 544/336 |
| 4,603,207 | 7/1986 | DiCosimo et al. | 546/286 |
| 4,931,561 | 6/1990 | Shimizu et al. | 544/336 |

FOREIGN PATENT DOCUMENTS 525367  2/1993  European Pat. Off. .

OTHER PUBLICATIONS

Reddy et al, *Chemical Abstracts*, vol. 123, No. 83313 (1995).

Forni et al, *Applied Catalysis*, 37, pp. 305–314 (1988).

*Primary Examiner*—Emily Bernhardt
*Attorney, Agent, or Firm*—Finnegan, Henderson, Farabow, Garrett & Dunner, L.L.P.

[57] ABSTRACT

This invention relates to a vapor phase process for preparing cyanopyrazine, in particular which is reacting 2-methylpyrazine with ammonia and oxygen over molybdenum-phosphorus oxide-based catalyst of the following formula having the high selectivity and conversion.

$$Mo_x P_y O_z \cdot X \cdot Y$$

wherein,

Mo is molybdenum;
P is phosphorus;
O is oxygen;
X is ammonium ion;
Y is water; and
x, y and z are respectively the numbers of atoms Mo, P and O, wherein y/x is 0.01 to 5 and z is 0.01 to 10.

2 Claims, No Drawings

PROCESS FOR PREPARING CYANOPYRAZINE

BACKGROUND OF THE INVENTION

1. Field of the Invention

This invention relates to a vapor phase process for preparing cyanopyrazine, in particular which is reacting 2-methylpyrazine with ammonia and oxygen over molybdenum-phosphorus oxide-based catalyst of the following formula having the high selectivity and conversion.

$$Mo_x P_y O_z X.Y$$

wherein,

Mo is molybdenum;

P is phosphorus;

O is oxygen;

X is ammonium salt or ion;

Y is water; and x,y and z are respectively the numbers of atoms Mo, P and O, wherein y/x is 0.01 to 5 and z is 0.01 to 10.

2. Description of Related Art

General process for preparing cyanopyrazine is following reaction scheme.

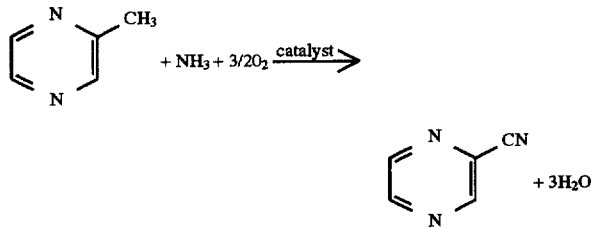

In the above reaction scheme, vanadium oxide supported in alumina or their mixture with the other various metal oxides such as antimony oxide, molybdenum oxide, iron oxide and tin oxide, etc., is used as a catalyst. For example, cyanopyrazine is prepared by ammoxidation in the mole ratio of 2-methylpyrazine: ammonia:air=1:4:50 or 2-methylpyrazine:ammonia:water:air=1:2:8.5:7.5 at 650~700K over antimony/vanadium/manganese oxide supported in alumina.

In this case, the conversion of 2-methylpyrazine is 90% and the selectivity for cyanopyrazine is 75% [ Applied Catalysis, Vol. 20, p219(1986)]. When preparing cyanopyrazine by ammoxidation in the molar feed ratio of 2-methylpyrazine:ammonia:air=1.9:5.0:189 or 2-methylpyrazine:ammonia:air:water=1.9:5.0:189:25.1 at 573~673K, atmosphere over antimony/vanadium/manganese oxide, the conversion of 2-methylpyrazine is less than 20%. [Applied Catalysis, Vol. 37, p305].

Vanadium oxide has been known as a catalyst to prepare not only cyanopyrazine but also cyanopyridine [Applied Catalysis, Vol. 83, p103(1992)].

Because nothing in the literature was known about methods for preparing cyanopyrazine except the above, methods have been studied for preparing cyanopyridine having similar structure with cyanopyrazine. As the result, kinds of using catalyst, reaction pathway and intermediate product, etc. of cyanopyridine are similar to cyanopyrazine's. For example, in 1986, Shimiz and Shinkichi et al. disclosed that when $VP_xSb_yO_z$ catalyst is used, the conversion of 3-methylpyridine is 98.7% and the selectivity of 3-cyanopyridine is 80% [European Patent No. 253, 360].

In 1989, A. Anderson disclosed that when vanadium/titanium oxide catalyst is used, the conversion of 3-methylpyridine is 100%, the selectivity for 3-cyanopyridine is 80%, the selectivities for carbon monoxide and carbon dioxide are 5% and the selectivity for tar is 15% [Journal of catalysis, Vol. 58, p283] Moreover A. Anderson, etc. have prepared 3-cyanopyridine by using vanadium oxide catalyst.

The above comparison is meaningless, because the conversion and selectivity represented in the preparation of cyanopyrazine or cyanopyridine of the above aren't compared under the same conditions. Commonly, when the conversion is 80~100%, the selectivity for 2-cyanopyrazine or cyanopyridine is 75~80%. This indicates that the selectivity for by-products such as methylpyridine, carbon monoxide, carbon dioxide and tar etc. is high. That is, while more reaction processes more by-product is formed over the catalyst such as the above.

Besides, during the ammoxidation of 2-methylpyrazine, by-products such as pyrazinamide and pyrazine etc. are formed. Accordingly the selectivity for cyanopyrazine as the desired product is closely related to the selectivities for pyrazinamide and pyrazine. But the selectivities for amides and other impurities are not discussed in the known method.

The inventors of this invention investigated new methods of preparing cyanopyrazine which can decrease the amount of ammonia used and can effectively decrease by-products by increasing the conversion of 2-methylpyrazine and the selectivity for cyanopyrazine. As a result, this invention is completed by ammoxidation of 2-methylpyrazine over a molybdenum-phosphorus oxide-based catalyst.

SUMMARY OF THE INVENTION

The object of this invention is to provide a new method for preparing cyanopyrazine which can decrease the amount of ammonia used and effectively decrease the production of by-product.

This invention relates to a method for preparing cyanopyrazine characterized by ammoxidation using 1 mole of 2-methylpyrazine, 1~20 moles of ammonia and 1.5~20 moles of oxygen over 0.1~10 g of the following formula at 573~873K.

$$Mo_x P_y O_z X.Y$$

wherein,

Mo, P, O, X, Y, x, y and z are respectively defined as the above-mentioned.

DETAILED DESCRIPTION OF THE INVENTION

This invention relates to a novel method for preparing cyanopyrazine which can decrease the amount of ammonia used and control production of by-products over a molybdenum-phosphorus oxide-based catalyst.

A patent for the catalyst of the above formula has been applied for in [U.S. Pat. No. 08/427,957 ], the method for preparing a catalyst of the above formular is as follows; Molybdenum salts are added into water, and completely dissolved at room temperature to 100° C. And, Phosphoric acid is added to the solution, heated with stirring. The solid precipitate formed is dried in an oven and pulverized to obtain a solid catalyst.

Specifically, a salt containing molybdenum, for example ammonium molybdate tetrahydrate $((NH_4)_6Mo_7O_{24}.H_2O)$, is added into water, and completely dissolved at the maximum temperature of 100° C. by slowly increasing the reaction temperature. And, phosphoric acid is added in the solution in order that y/x, an atomic ratio of phosphorus to molybdenum, is 0.01~5. Then, if y/x is less than 0.01, the desired reaction activity cannot be obtained, and if y/x is more than 5, the hygroscopic property of the catalyst itself is too high because of the addition of excessive phosphoric acid and thus the reactivity is decreased. Therefore, in this invention, in order to accelerate the reaction rate and easily remove residue, the temperature of the above reaction solution should be raised by 50°~10° C., and then water is removed during the reaction under stirring to concentrate the reactant, thereby the desired product is obtained as the bulk solid.

According to this invention, the bulk solid may be dried for 1–15 hours in an oven at 30°~150° C. and pulverized to be effectively used as a catalyst. The pulverized powder is kept in an airtight desiccator to prevent from contacting with water in the atmosphere. The more y/x of the pulverized powder is decreased, the more the color is white, and the more y/x is increased, the more the color is light green and the hygroscopic property is increased.

To activate the catalyst, a sintered quartz reactor is filled with catalyst, and then nitrogen gas is flowed in at 4 l/hr of flow rate and pretreatment is carried out at higher than 573K for 2~6 hours. If pretreatment temperature of a catalyst is lower than 573K, the catalyst isn't sufficiently activated.

2-Methylpyrazine, ammonia and oxygen are added to the pretreated catalyst and ammoxidation results in cyanopyrazine as the desired product at 573~873K. Total amount of gas inflow is 0.5~10 l/hr. If reaction temperature is lower than 573K, the conversion of 2-methylpyrazine is inactivated and if it is higher than 873K, the selectivity for cyanopyrazine is lower by forming impurities such as amide, carbon monoxide, carbon dioxide and tar etc., by excess oxidation.

In the above process for preparing cyanopyrazine, 0.1~10 g of a catalyst, 1~20moles of ammonia and 1.5~20 moles of oxygen to 1 mole of 2-methylpyrazine are used.

But change of the conversion and selectivity as increasing the amount used of a catalyst is very small. Accordingly, it is to be desired that the amount used of a catalyst is the same with the above range. An especially outstanding feature is that just 1 mole equivalent of expensive ammonia to 2-methylpyrazine can show sufficient selectivity and conversion.

Characteristics of the catalyst both before and after pretreatment, after reaction are confirmed by BET surface area measurment, pore volume measurment, infrared spectrometer, thermal gravimetric spectrometer, X-ray diffraction analyzer, X-ray fluorescence spectroscope and wet analysis of molybdenum and phosphorus. The conversion and selectivity to represent activation of a catalyst is put into the following equations (2) and (3).

$$\text{Conversion (\%)} = \frac{\text{Moles of the reacted 2-methylpyrazine}}{\text{Moles of the supplied 2-methylpyrazine}} \times 100 \quad (2)$$

$$\text{Selectivity (\%)} = \frac{\text{Moles of the produced compound}}{\text{Moles of the reacted 2-methylpyrazine}} \times 100 \quad (3)$$

This invention may be illustrated in more detail as following examples, but it is not limited by the examples.

EXAMPLE 1

In order to pretreat a catalyst, a quartz reactor (16 mm diameter, 200 mm length) with a sintered quartz was filled with 0.5 g of $Mo_x.P_y.O_z.X.Y$(y/x=0.75), and s then nitrogen gas was flowed into the reactor at 4 l/hr of the flow rate, 4K/min of the raising temperature rate, at 773K for 4 hours.

The feed to the reactor contains 2-methylpyrazine, ammonia and oxygen, the mole ratio of 2-methylpyrazine:ammonia:oxygen is 1:6:6, and then reacted at each 563K, 583K, 593K, 603K, 613K, 619K, 623K, 633K, 643K, 883K, for 24 hours. As the result cyanopyrazine was obtained.

The produced cyanopyrazine was analyzed by on-line gas chromatograph and confirmed by standard material. The conversion and selectivity for 2-methylpyrazine according to the above reaction temperature were given in the following Table 1.

TABLE 1

| Reaction Temperature(K.) | Conversion(%) | Selectivity(%) | | | |
|---|---|---|---|---|---|
| | | cyanopyrazine | pyrazinamide | pyrazine | by-products |
| 563 | 10.2 | 90.6 | 1.0 | 0 | 8.4 |
| 583 | 16.1 | 93.2 | 1.9 | 0 | 4.9 |
| 593 | 23.8 | 95.1 | 1.5 | 0 | 3.4 |
| 603 | 36.7 | 93.6 | 4.0 | 0 | 2.4 |
| 613 | 56.4 | 93.4 | 4.7 | 0.4 | 1.5 |
| 619 | 71.1 | 93.6 | 4.9 | 0.4 | 1.1 |
| 623 | 79.9 | 93.2 | 4.9 | 0.8 | 1.1 |
| 633 | 96.2 | 92.1 | 4.0 | 3.2 | 0.7 |
| 643 | 99.1 | 89.7 | 5.1 | 4.6 | 0.6 |
| 883 | 59.0 | 54.1 | 0 | 0 | 45.9 |

As the above results show, when cyanopyrazine of this invention is prepared, if reaction temperature was beyond the range of 573~873K, the conversions of 2-methylpyrazine were abruptly decreased. Especially when reaction temperature was higher than 873K, the selectivity for cyanopyrazine was abruptly decreased.

Within the range of 573~873K, the more reaction temperature was increased, the more the conversion of 2-methylpyrazine and the selectivity for cyanopyrazine was slowly increased. At 643K, the conversion was the highest at 99.1%. Also, the selectivity for by-products was slowly decreased reaction temperature increased and the selectivity was the lowest at 0.6% at 643K.

EXAMPLE 2

Cyanopyrazine was prepared by using the method described in the above Example 1 except that 1 mole of 2-methylpyrazine and 6 moles of ammonia were used and moles of oxygen were varied.

The conversion of 2-methylpyrazine and the selectivity for the product according to the amount used of oxygen are given in the following Table 2.

TABLE 2

| Oxygen (mole) | Conversion(%) | Selectivity(%) | | | |
|---|---|---|---|---|---|
| | | cyanopyrazine | pyrazinamide | pyrazine | by-products |
| 1.2 | 11.8 | 93.4 | 0 | 0.2 | 6.4 |
| 2.4 | 56.0 | 96.7 | 1.5 | 0.5 | 1.3 |
| 3.6 | 86.9 | 97.1 | 0.9 | 1.2 | 0.8 |
| 4.8 | 96.3 | 95.3 | 1.0 | 2.9 | 0.8 |
| 7.2 | 99.7 | 88.4 | 1.7 | 9.3 | 0.6 |
| 8.4 | 99.8 | 88.2 | 2.0 | 9.2 | 0.6 |
| 24.0 | 89.8 | 54.2 | 20.1 | 9.2 | 16.5 |

As the above results show, when moles of oxygen was beyond the range of 1.5~20 moles, that is, if it was less than 1.5 moles, the conversion of 2-methylpyrazine was abruptly decreased because the reaction was not completed. If it was more than 20 moles, the selectivity for cyanopyrazine was decreased because much by-products was produced by oxidation.

2-Methylpyrazine, ammonia and oxygen are added to the pretreated catalyst and ammoxidation proceeds to obtain cyanopyrazine as the desired product at 573~873K.

In range of 1.5~20 moles of oxygen, the more the amount of oxygen used was increased, the more the conversion of 2-methylpyrazine was increased. But, if moles of oxygen was more than 3.6 moles the selectivity for cyanopyrazine was decreased.

EXAMPLE 3

Cyanopyrazine was prepared by using the method described in the above Example 1 except that 1 mole of 2-methylpyrazine and 6 moles of oxygen were used and moles of ammonia were varied. The conversion of 2-methylpyrazine and the selectivity of the product according to the amount of ammonia used are given in the following Table 3.

TABLE 3

| Ammonia (mole) | Conversion(%) | Selectivity(%) | | | |
|---|---|---|---|---|---|
| | | cyanopyrazine | pyrazinamide | pyrazine | by-products |
| 0.5 | 37.5 | 94.6 | 1.6 | 2.8 | 1.0 |
| 1.0 | 95.3 | 95.2 | 1.9 | 2.0 | 0.9 |
| 1.2 | 96.4 | 95.3 | 2.0 | 2.3 | 0.4 |
| 2.4 | 97.3 | 95.4 | 1.6 | 2.4 | 0.6 |
| 3.6 | 97.9 | 95.6 | 1.1 | 2.7 | 0.6 |
| 4.8 | 98.5 | 93.2 | 2.8 | 3.4 | 0.6 |
| 6.0 | 98.7 | 91.8 | 3.2 | 4.3 | 0.7 |
| 7.2 | 98.5 | 92.2 | 2.8 | 4.4 | 0.6 |
| 8.4 | 99.1 | 92.0 | 3.0 | 4.3 | 0.7 |
| 24.0 | 99.4 | 91.5 | 3.6 | 4.3 | 0.6 |

As the above results show, when moles of ammonia was beyond the range of of 1~20 moles, that is, if the amount of ammonia used was less than 1 mole, the conversion of 2-methylpyrazine was low, and if it is more than 20 moles, change of the conversion and selectivity did not occur. Accordingly, it was not economical to use of excess ammonia.

And, commonly, when the excess ammonia was fed over stoichiometric amount, i.e. over 1 mole, change of the conversion or selectivity by increasing the amount of ammonia fed did not occur. Accordingly, in the preparing method, the sufficient effect can be shown even if 1 mole of expensive ammonia is used.

As the above results of Example 1~3 show, the conversion and selectivity according to this invention is higher than in the known ammoxidation of 2-methylpyrazine and can decrease production of by-products.

What is claimed is:

1. A method for preparing cyanopyrazine by ammoxidation comprising reacting 1 mole of 2-methylpyrazine, 1~20 moles of ammonia and 1.5~20 moles of oxygen over 0.1~10 g of the following formula catalyst at 573~873K:

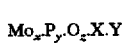

wherein,

Mo is molybdenum;

P is phosphorus;

O is oxygen;

X is ammonium ion;

Y is water; and x, y and z are respectively the numbers of atoms Mo, P and O, wherein y/x is 0.01 to 5 and z is 0.01 to 10.

2. The method according to claim 1, wherein said catalyst is pretreated under nitrogen gas at 4 l/hr of the flow rate, at over 573K, for 2~6 hours.

* * * * *

UNITED STATES PATENT AND TRADEMARK OFFICE
CERTIFICATE OF CORRECTION

PATENT NO. : 5,786,478
DATED : July 28, 1998
INVENTOR(S) : Young K. LEE et al.

It is certified that error appears in the above-identified patent and that said Letters Patent is hereby corrected as shown below:

TITLE PAGE:

Item [57], line 7 of Abstract, , "$Mo_x.P_y.O_z.X.Y$" should read --$Mo_x \cdot P_y \cdot O_z \cdot X \cdot Y$--.

Col. 1, line 12 and col. 2, line 45, "$Mo_x.P_y.O_z.X.Y$" should read --$Mo_x \cdot P_y \cdot O_z \cdot X \cdot Y$--.

IN THE CLAIMS:

Claim 1, Col. 6, line 66, "$Mo_x.P_y.O_z.X.Y$" should read --$Mo_x \cdot P_y \cdot O_z \cdot X \cdot Y$--.

Signed and Sealed this

Thirteenth Day of October 1998

Attest:

BRUCE LEHMAN

*Attesting Officer*    *Commissioner of Patents and Trademarks*